United States Patent
Karpus et al.

(10) Patent No.: US 12,188,013 B2
(45) Date of Patent: Jan. 7, 2025

(54) CATALYTIC BIOMOLECULE ACTIVITY RECORDING INTO DNA SEQUENCE

(71) Applicants: Vilnius University, Vilnius (LT); UAB Biomatter Designs, Vilnius (LT)

(72) Inventors: Laurynas Karpus, Vilnius (LT); Ignas Mazelis, Vilnius (LT); Irmantas Rokaitis, Vilnius (LT); Vykintas Jauniskis, Vilnius (LT); Rolandas Meskys, Vilnius (LT)

(73) Assignees: Vilnius University, Vilnius (LT); UAB Biomatter Designs, Vilnius (LT)

( * ) Notice: Subject to any disclaimer, the term of this patent is extended or adjusted under 35 U.S.C. 154(b) by 944 days.

(21) Appl. No.: 17/283,968

(22) PCT Filed: Oct. 8, 2019

(86) PCT No.: PCT/IB2019/058545
§ 371 (c)(1),
(2) Date: Apr. 9, 2021

(87) PCT Pub. No.: WO2020/075055
PCT Pub. Date: Apr. 16, 2020

(65) Prior Publication Data
US 2021/0355486 A1    Nov. 18, 2021

(30) Foreign Application Priority Data

Oct. 10, 2018  (LT) ................ PA2018 542

(51) Int. Cl.
*C12N 15/10*  (2006.01)
*C12Q 1/44*  (2006.01)
*C12Q 1/6806*  (2018.01)

(52) U.S. Cl.
CPC .......... *C12N 15/1075* (2013.01); *C12Q 1/44* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 6,537,783 B1 * | 3/2003 | Guillou-Bonnici | C07H 19/06 536/25.3 |
| 7,708,949 B2 | 5/2010 | Stone et al. | |
| 8,337,778 B2 | 12/2012 | Stone et al. | |
| 8,765,485 B2 | 7/2014 | Link et al. | |
| 9,002,043 B2 | 4/2015 | Norris et al. | |
| 9,667,173 B1 | 5/2017 | Kappus | |
| 2015/0057525 A1 | 2/2015 | Tomiha | |
| 2015/0104026 A1 | 4/2015 | Kappus | |

FOREIGN PATENT DOCUMENTS

| | | |
|---|---|---|
| WO | 20020022869 A2 | 3/2002 |
| WO | 20040091763 A2 | 10/2004 |
| WO | 20060096571 A2 | 9/2006 |
| WO | 20080024052 A1 | 2/2008 |

OTHER PUBLICATIONS

Autour, Alexis, and Michael Ryckelynck. 2017. 'Ultrahigh-Throughput Improvement and Discovery of Enzymes Using Droplet-Based Microfluidic Screening'. Edited by Andrew J deMello and Xavier Casadevall i Solvas. Micromachines 8 (4): 128.
Baret, Jean-Christophe, Oliver J. Miller, Valerie Taly, Michaël Ryckelynck, Abdeslam El-Harrak, Lucas Frenz, Christian Rick, et al. 2009. 'Fluorescence-Activated Droplet Sorting (FADS): Efficient Microfluidic Cell Sorting Based on Enzymatic Activity'. Lab on a Chip 9 (13): 1850-58.
Böttcher, Dominique, Patrick Zägel, Marlen Schmidt, and Uwe T. Bornscheuer. 2017. 'A Microtiter Plate-Based Assay to Screen for Active and Stereoselective Hydrolytic Enzymes in Enzyme Libraries'. In Metagenomics: Methods and Protocols, edited by Wolfgang R. Streit and Rolf Daniel, 197-204. New York, NY: Springer New York.
Currin, Andrew, Neil Swainston, Philip J Day, and Douglas B Kell. 2015. 'Synthetic Biology for the Directed Evolution of Protein Biocatalysts: Navigating Sequence Space Intelligently'. Chemical Society Reviews 44 (5): 1172-1239.
Illanes, Andrés, Ana Cauerhff, Lorena Wilson, and Guillermo R. Castro. 2012. 'Recent Trends in Biocatalysis Engineering'. Biocatalysis 115 (July): 48-57. https://doi.org/10.1016/j.biortech.2011.12.050.
Keasling, Jay D. 2012. 'Synthetic Biology and the Development of Tools for Metabolic Engineering'. Synthetic Biology: New Methodologies and Applications for Metabolic Engineering 14 (3): 189-95.
Shoda, Shin-ichiro, Hiroshi Uyama, Jun-ichi Kadokawa, Shunsaku Kimura, and Shiro Kobayashi. 2016. 'Enzymes as Green Catalysts for Precision Macromolecular Synthesis'. Chemical Reviews 116 (4): 2307-2413. https://doi.org/10.1021/acs.chemrev.5b00472.
Wessely, Frank, Martin Bartl, Reinhard Guthke, Pu Li, Stefan Schuster, and Christoph Kaleta. 2011. 'Optimal Regulatory Strategies for Metabolic Pathways in *Escherichia coli* Depending on Protein Costs'. Molecular Systems Biology 7 (July): 515-515.
Xiao, Han, Zehua Bao, and Huimin Zhao. 2015. 'High Throughput Screening and Selection Methods for Directed Enzyme Evolution'. Industrial & Engineering Chemistry Research 54 (16): 4011-20.
International Search Report and Written Opinion mailed Jan. 21, 2010 for PCT Application No. PCT/IB2019/058545.
International Search Report and Written Opinion mailed Jul. 10, 2019 for PCT Application No. PCT/IB2018/055860.

* cited by examiner

*Primary Examiner* — Samuel C Woolwine
(74) *Attorney, Agent, or Firm* — Koivula & Somersalo, LLC

(57) ABSTRACT

The present invention relates to catalytic biomolecule characterization and microfluidics. It is used for identification of nucleic acids encoding active catalytic molecules in the plurality of nucleic acids and for gathering information about catalytic biomolecule activity. It can also be used for exploring different properties of regulating sequences that modulate expression of catalytic biomolecules by recording that information into the DNA sequence of the same catalytic biomolecule using microfluidic techniques.

20 Claims, 5 Drawing Sheets

Specification includes a Sequence Listing.

CATALYTIC BIOMOLECULE ACTIVITY RECORDING INTO DNA SEQUENCE

CROSS REFERENCE TO RELATED APPLICATIONS

This application claims the benefit of Lithuanian Application No. LT2018 542, filed Oct. 10, 2018, the contents of which are hereby incorporated in its entirety. This application is a national stage entry of International Application No. PCT/IB2019/058545, the contents of which are hereby incorporated in its entirety.

SEQUENCE LISTING

A Sequence Listing is hereby incorporated by reference. Said Sequence Listing has been filed as an electronic document, created on Oct. 10, 2018 is entitled "V8355-seql-000001.txt", and is 4,674 bytes in size.

FIELD OF THE INVENTION

The present invention generally relates to catalytic biomolecule characterization and microfluidics.

BACKGROUND OF THE INVENTION

The ultimate goal of applied chemistry is the cost-effective production of valuable chemical compounds on demand. Synthetic biology and metabolic engineering show immense potential, enabling multi-step synthesis of complex molecules without the need of purification of intermediates. Additionally, biocatalysts used in those metabolic pathways can offer an enormous 17 orders of magnitude chemical reaction acceleration as well as excellent stereo-, chemo- and regio-selectivity in aqueous environments at ambient temperature and pressure. Synthetic metabolic pathways rely on two major things-precisely engineered enzymes (or biocatalysts) which catalyze every step of compound transformation and well-characterized genetic regulatory sequences which tightly regulate the expression of specific enzymes to create an efficient metabolic pathway.

Currently, one of the main problems in synthetic biology and metabolic engineering is that for many important chemical reactions, efficient enzymes have not yet been discovered or engineered. Identifying enzyme amino acid sequence with the required novel or optimized function is a challenging task because the sequence space is incomprehensibly large. A protein made from 300 amino acid residues has more than $10^{390}$ possible sequence variants. Additionally the fraction of functional sequences in such space may be as low as $10^{-77}$. Machine learning algorithms now offer a way to solve these complex sequence-function problems, yet they require a high amount of good quality sequence-activity data collected from screening assays. Currently, available state of the art screening and selection methods allow screening the activity of a large number of catalytic biomolecules in a high-throughput manner. However, specific catalytic activity of certain biomolecule can be attributed to the particular nucleic acid sequence encoding said molecule only for a small fraction of sequences within the screened library.

Two good examples of current state of the art methods are droplet microfluidic and microchamber array technologies. Though both of these technologies offer high-throughput screening (up to $10^7$ individual measurements for droplet microfluidics and correspondingly $10^{5-6}$ for microchamber arrays), they both suffer from inability to pair the screened signal with biomolecule's sequence that has originated the signal. Droplet microfluidics is based on encapsulating biomolecules into picoliter droplets which then act as tiny microreactors. These droplets can be sorted based on their output signal once it reaches a certain pre-set detection threshold. Yet, a substantial drawback of such approach is that the population of droplets containing catalytic biomolecules that did not produce a certain signal threshold is lost. On the other hand, the biomolecules within the droplets that did reach the detection threshold are usually pooled together and analyzed by DNA sequencing. After such analysis it is impossible to correlate specific activity of each mutant biomolecule to its original sequence in a high-throughput manner. Furthermore, droplet microfluidic based methods are mostly limited to assays using fluorogenic substrates. In contrast, microchamber arrays are usually employed with robotic systems which can screen individual mutant containing microwells in order to detect catalytic activity. Such systems allow acquiring the information about the activity in each microwell as well as its precise location within the microarray. However, it is currently prohibitively expensive and time consuming to extract the content of a specific microwell after the initial activity screening in a high-throughput manner in order to assess all of their function to sequence relationship. Therefore, novel screening technologies that are able to efficiently collect the information about sequence-function (genotype-phenotype) relationship in an ultrahigh-throughput manner are necessary in order to accelerate protein and metabolic engineering with the help of machine learning algorithms.

SUMMARY OF INVENTION

The present invention generally relates to microfluidics, modified nucleotides and biomolecule activity and interaction recording. For example, certain aspects are generally directed to systems and methods for assessing catalytic biomolecule activity by recording that information into the DNA sequence of the same catalytic biomolecule using microfluidic techniques.

In one set of embodiments, a plurality of genetic information carriers may be encapsulated into microfluidic droplets. The encapsulation is performed in order to perform different reactions in separate compartments. These genetic information carriers may be provided in the form of DNA, RNA or nucleic acids within the cells and they may contain sufficient information to produce a catalytic biomolecule.

In another set of embodiments, the genetic information carriers may also encode genetic regulatory sequences that may be required to express a catalytic biomolecule using that genetic information carrier. In some cases, different genetic regulatory sequences may affect the concentration or activity of catalytic biomolecule produced in the droplet.

In another set of embodiments, catalytic biomolecule may be the peptide, the enzyme protein or the RNA ribozyme capable of bio-catalysis.

In one set of embodiments, together with genetic information carriers, a plurality of natural or chemically modified nucleotides (substrate nucleotides) may also be encapsulated into the droplets. In some cases, these substrate nucleotides may serve as substrates for catalytic biomolecules. For example, when catalytic biomolecules are being produced or provided in the microfluidic droplet together with substrate nucleotides, catalytic biomolecules may recognize those substrate nucleotides and catalyze chemical conversion of the substrate.

In another set of embodiments, after catalytic biomolecule performs the chemical conversion of at least some of the substrate nucleotides within the compartment, nucleic acid synthesis or amplification may be initiated in at least some of the droplets by providing all components necessary for such synthesis reaction, such as polymerase, nucleotides, primers and buffer components. In addition, reference nucleotides may be provided, which do not act as a target for catalytic biomolecules, but instead can help to determine the amount of chemically converted substrate nucleotides (modified substrate nucleotides).

Important aspect of this invention is that after the chemical conversion of substrate nucleotides, the substrate and/or modified substrate and/or reference nucleotides may be incorporated into the nascent nucleic acid strand produced by the polymerase enzyme. This way during nucleic acid synthesis or amplification following the catalysis reaction certain amount of substrate and/or modified substrate and/or reference nucleotides are incorporated into newly synthesized nucleic acid strand and thereby reflect the level of activity of the catalytic biomolecule within the droplet. In some cases, the template for amplification or nucleic acid synthesis may be the same DNA template from which the catalytic biomolecule was produced in the droplet. In some embodiments, the template for amplification or nucleic acid synthesis may be the RNA molecule encoding catalytic ribozyme biomolecule produced in the droplet from the genetic information carrier.

In one set of embodiments, the amplified nucleic acid fragments in the droplet may contain a specific ratio of substrate and/or modified substrate and/or reference nucleotides reflecting certain level of activity of catalytic biomolecule. These fragments may be sequenced using methods for single molecule sequencing and the information about specific catalytic biomolecule sequence and the flanking genetic regulatory sequences may be retrieved. Also the substrate and/or modified substrate and/or reference nucleotides may also be identified in the sequenced nucleic acid fragments using single molecule sequencing methods. The information about the amount of different types of nucleotides within the fragment may be correlated with specific activity of particular catalytic biomolecule present in the certain droplet. By that logic, billions of different catalytic biomolecules can have their catalytic activity recorded in DNA sequence. As this information is retrieved, it is possible to correlate relative catalytic activity of each mutant biomolecule within the library with a nucleic acid sequence encoding said mutant. Such method may be expanded to libraries of billions of catalytic biomolecule mutants swiftly and efficiently without the increase of time needed to perform such method.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numerical. For purposes of clarity, not every component is labelled in every figure, or is every component of each embodiment of the invention shown where illustration is not necessary to allow those of ordinary skill in the art to understand the invention. In the figures.

DETAILED DESCRIPTION OF THE INVENTION

Figure 1:
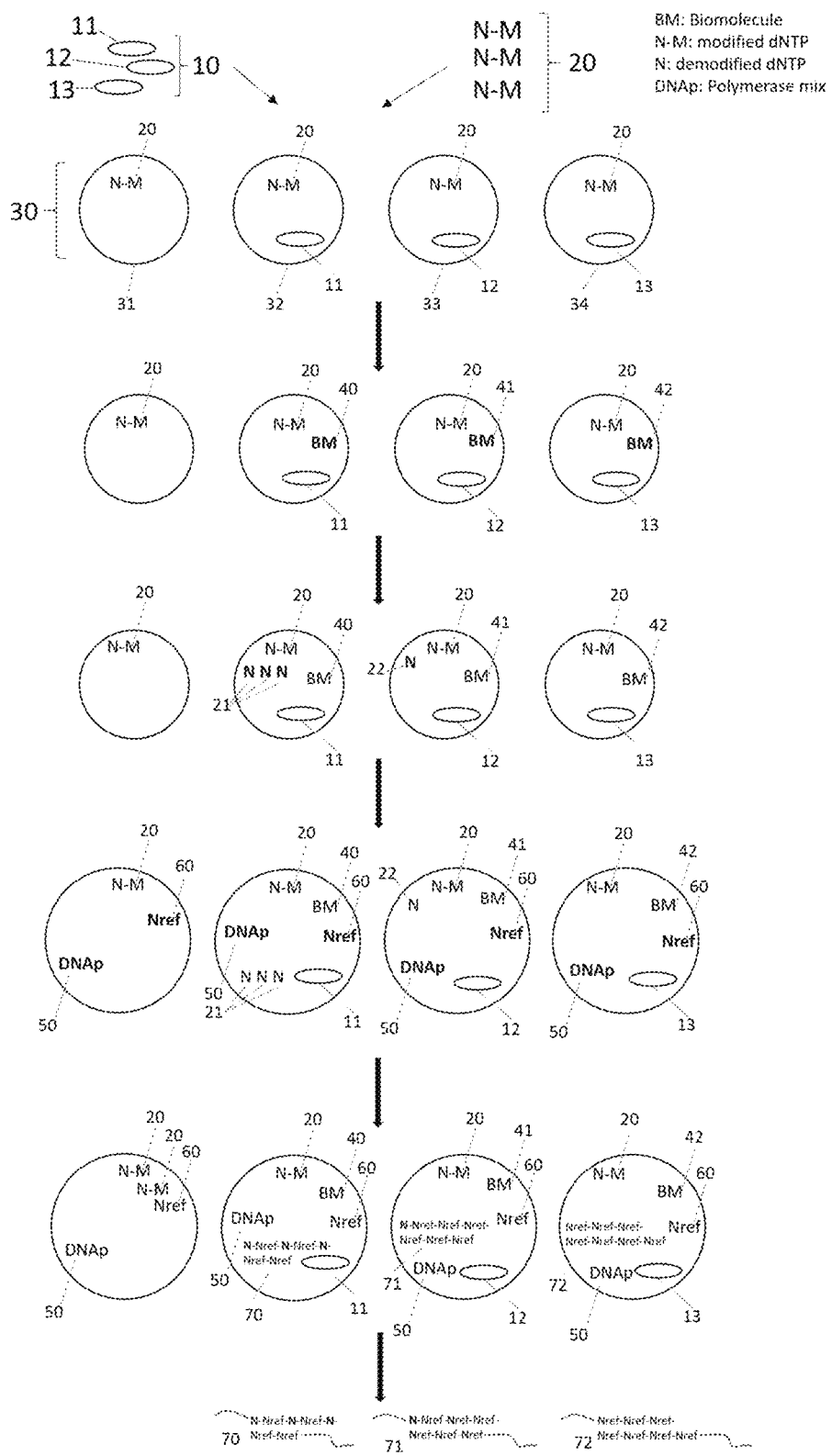
FIG. 1 illustrates a flowchart in accordance with one embodiment of the invention.

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the scope of the invention.

Throughout this disclosure, various aspects of this invention can be presented in a range format. It should be understood that the description in range format is merely for convenience and brevity and should not be construed as an inflexible limitation on the scope of the invention.

Definitions

To aid in understanding the invention, several terms are defined below.

Unless defined otherwise, all technical and scientific terms used herein have the same meaning as commonly understood by a person skilled in the art. Although any methods and materials similar to or equivalent to those described herein can be used in the practice or testing of the claims, the exemplary methods and materials are described herein.

The terms "comprising", "having", "including", and "containing" are to be construed as open-ended terms (i.e., meaning "including, but not limited to") unless otherwise noted.

The terms "nucleic acid" and "oligonucleotide" as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogues in which the base, sugar or phosphate backbone is modified as well as non-purine or non-pyrimidine nucleotide analogues.

The term "promoter" as used herein, refers to a cis-acting DNA sequence that directs RNA polymerase and other trans-acting transcription factors to initiate RNA transcription from the DNA template that includes the cis-acting DNA sequence.

The term "genetic information carrier" as used herein, refers to a biomolecule that contains the information required to synthesize a catalytic biomolecule. Said biomolecule may exist in the isolated form in vitro or within the cell in case mutagenized cell library is used.

The term "repressor protein" or "repressor" as used herein, refers to a protein that binds to operator of DNA or to RNA to prevent transcription or translation, respectively.

The term "operator" as used herein, refers to a site on DNA at which a repressor protein binds to prevent transcription from initiating at the adjacent promoter.

The term "transcription terminator sequence" or "terminator" as used herein, refers to a signal within DNA that functions to stop RNA synthesis at a specific point along the DNA template. A transcription terminator may be either rho factor dependent or independent. An example of a transcription terminator sequence is the T7 terminator. Transcription terminators are known in the art and may be isolated from commercially available vectors according to recombinant methods known in the art.

The term "activation" as used herein, refers to enhancement of transcription or translation by binding of activator protein to specific site on DNA or mRNA. Preferably, activation includes a significant change in transcription or translation level of at least 1.5 fold, more preferably at least two fold, and even more preferably at least five fold.

The term "resolved DNA" as used herein, refers to the sequencing of DNA molecule, wherein the information about the nucleotide sequence modification pattern of DNA molecule is gained.

The term "error-prone PCR" as used herein, refers to the use of PCR under conditions in which misincorporation of nucleotides is favored, for example where random mutants are sought for a portion of amplified DNA.

The term "ribozyme" as used herein, refers to an RNA molecule with catalytic activity.

The term "riboswitch" as used herein, refers to a cis-regulatory RNA element that regulates expression of a downstream or upstream gene in response to a specific ligand molecule.

The term "catalytic biomolecule" as used herein, refers to any biomolecule that catalyzes specific chemical or biochemical reaction. The catalytic biomolecule may be a protein enzyme, ribozyme or a deoxyribozyme. For use in the present invention, catalytic biomolecule catalyzes the chemical conversion of the substrate nucleotide.

The term "nucleic acid molecule encoding catalytic biomolecule" as used herein, refers to any nucleic acid biopolymer that encodes the information required to synthesize or produce a catalytic biomolecule.

The term "ribosome binding site" (RBS) as used herein, refers to a nucleotide sequence near the 5' terminus of mRNA required for binding of mRNA to the small ribosomal subunit.

The term "nucleic acid synthesis reaction" refers to any chemical reaction, including an enzymatic reaction, which results in increased copies of a template nucleic acid sequence or results in transcription of a template nucleic acid. Nucleic acid synthesis reactions include amplification reactions such as reverse transcription, the polymerase chain reaction (PCR), including Real Time PCR Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step. There are also single step amplification reactions, which usually operate at constant temperature, such as multiple displacement amplification reaction. The multiple displacement amplification (MDA) generally involves bringing into contact a set of primers, DNA polymerase, and a template, and incubating the target sample under conditions that promote replication of the template sequence. The template is not subjected to denaturing conditions. It was discovered that elimination of a denaturation step and denaturation conditions has additional advantages such as reducing sequence bias in the amplified products. The primers can be hexamer primers.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, *Bacillus stearothermophilus* (Bst) DNA Polymerase large fragment, *Bacillus subtilis* (Bsu) DNA polymerase Large fragment, Bacteriophage Φ29 (phi29) DNA polymerase among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "reaction mixture" as used herein, refers to a solution containing reagents necessary to carry out a given reaction. A "nucleic acid synthesis reaction mixture", which refers to a solution containing reagents necessary to carry out an nucleic acid synthesis reaction, typically contains oligonucleotide primers and a DNA polymerase in a suitable buffer. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

The term "droplet enrichment" as used herein, refers to addition of chemical reagents to an already formed microfluidic droplets.

The term "substrate nucleotide" as used herein, refers to a deoxyribonucleotide triphosphate or ribonucleotide triphosphate which is capable to act as a substrate for a catalytic biomolecule. Substrate nucleotide may or may not have additional chemical modifications. For example, such modifications may be added to nucleotides via various linking groups known to the person skilled in the art or may be known as naturally available nucleotides or modifications thereof.

The term "modified substrate nucleotide" as used herein, refers to a chemically converted substrate nucleotide by a catalytic biomolecule.

The term "reference nucleotide" as used herein, refers to a deoxyribonucleotide triphosphate, or ribonucleotide triphosphate which does not act as a substrate for a catalytic biomolecule and is different both from the substrate nucleotide and modified substrate nucleotide.

In some embodiments, the compartments may be droplets, such as microfluidic droplets. Those of ordinary skill in the art will be aware of techniques for encapsulating particles within microfluidic droplets; see, for example, U.S. Pat. Nos. 7,708,949; 8,337,778; 8,765,485, or Int. Pat. Apl. Pub. NOs. WO 2004/091763 and WO 2006/096571, each incorporated herein by reference. In some cases, the particles may be encapsulated at a density of less than 1 particle/droplet (and in some cases, much less than 1 particle/droplet) to ensure that most or all of the droplets have only zero or one particle present in them. A droplet can be a small volume of a first liquid that is encapsulated by an immiscible second liquid, such as a continuous phase of an emulsion (and/or by a larger droplet). The volume of a droplet, and/or the average volume of droplets in an emulsion, can, for example, be less than about one microliter (or between about one microliter and one nanoliter or between about one microliter and one picoliter), less than about one nanoliter (or between about one nanoliter and one picoliter), or less than about one picoliter (or between about one picoliter and one femtoliter), among others. A droplet can be spherical or non-spherical. A droplet can be a simple droplet or a compound droplet. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase.

Catalytic Biomolecule Activity Recording

The present invention generally relates to microfluidics, modified nucleotides and biomolecule activity and interaction recording.

Certain aspects of the invention are generally directed to systems and methods for assessing catalytic biomolecule activity by recording that information into the DNA sequence encoding the same catalytic biomolecule using microfluidic technologies. In one set of embodiments, a plurality of genetic information carriers may be encapsulated into microfluidic droplets or other suitable compartments, for example, microwells of a microwell plate, individual spots on a slide or other surface, or the like. The encapsulation is employed in order to perform different reactions in separate compartments. These genetic information carriers may be provided in the form of nucleic acids such as DNA, RNA or alternatively cells and they may contain the sufficient information to produce a catalytic biomolecule. The nucleic acids may arise from lysed cells or other material within the droplets.

For example, if genetic information carriers in the form of DNA are encapsulated into microfluidic droplets, a cell-free protein expression reagents may also be incorporated in that droplet in order to synthesize the catalytic biomolecule. In another example, if cells are the genetic information carriers and are encapsulated in microfluidic droplets, lysis reagents may be added in order to lyse the cells. Cells lysed in droplet may release catalytic biomolecule DNA template and/or synthesized catalytic biomolecule.

In one set of embodiments, the catalytic biomolecule encoded by genetic information carriers may be DNA, RNA or protein molecule. In cases where the catalytic biomolecule is DNAzyme, no protein expression reagents may be required, as DNA is the catalytic biomolecule itself. In some cases, RNA catalytic biomolecule or ribozyme can be produced using in vitro transcription reagents.

In another set of embodiments, the genetic information carriers may also encode genetic regulatory sequences that may be required to express a catalytic biomolecule using that genetic information carrier. In some cases, different genetic regulatory sequences may affect the concentration or activity of catalytic biomolecule produced in the droplet. These regulatory sequences may be ribosome binding site, promoter sequence, ribozyme, riboswitch, transcription enhancer, operator, repressor binding site, activator binding site, DNA binding site, terminator, repressor encoding gene, activator encoding gene.

In one set of embodiments, together with genetic information carriers, a plurality of nucleotides may also be encapsulated into the droplets. For example, these nucleotides may be deoxyribonucleoside or deoxyribonucleoside triphosphates. In another example, these nucleotides can be naturally occurring major nucleotides or chemically modified nucleotides.

In one set of embodiments, nucleotides used in such system may consist of one of purine (e.g. adenine, guanine, hypoxanthine or any variations thereof) or pyrimidine (cytosine, thymine, uracil or any variations thereof) nucleobases and triphosphate. The modified nucleotide may contain additional chemical group that is not present in the natural nucleosides (i.e., adenosine, guanosine, cytidine, thymidine, uridine). For example, one or more substituent groups may be added to the base, sugar or phosphate moieties of the nucleotide. On the other hand, one or more substituents may be deleted from the base, sugar or phosphate moiety. Or, one or more atoms or substituents may be substituted for one or more others in the nucleotide. A modified nucleotide may also be a molecule that resembles a natural nucleotide little, if at all. Further, any of the hydroxyl groups ordinary present on the sugar (e.g., ribose, deoxyribose or other) of a nucleotide may be replaced by a phosphate group or by protecting groups; or substituted with amines or other organic functional groups. Nucleotides may also contain analogous forms of ribose or deoxyribose sugars, including 2' (3')-O-methyl-, 2' (3')-O-allyl-, 2' (3')-O-ethyl-, 2' (3')-O-propyl-, 2' (3')-metoxyethyl-, 2' (3')-fluoro-pentoses, α-anomeric sugars, other aldopentoses (i.e., arabinoses, xyloses, lyxoses), pyranoses, acyclic analogues. Also, a ribose or deoxyribose sugar moiety may have a removable 3'-OH blocking group covalently attached thereto, such that the 3' carbon atom has attached a group of the structure —O—R wherein R is any of an alkyl, substituted alkyl, arylalkyl, alkenyl, alkynyl, aryl, heteroaryl, heterocyclic, acyl, cyano, alkoxy, aryloxy, heteroaryloxy or amido group. In some aspects, a nucleotide may comprise at least one base selected from the group consisting of 5-methylcytosine, 5-aza-cytosine, N4-acetylcytosine, N4-benzoylcytosine, 5-formylcytosine, N4-methylcytosine, 5-hydroxymethylcytosine, 2-thio-cytosine, 2-thio-5-methyl-cytosine, 5-methoxyuracil, 2-thiouracil, 4-thiouracil, N6-methyladenine, N6-isopentenyladenine, N6-(cis-hydroxyisopentenyl) adenine, N6-glycinylcarbamoyladenine, N6-threonylcarbamoyladenine, N2-methylguanine. In some cases, a nucleotide may contain a cytosine base having a group covalently attached thereto, such that the N4 atom has attached a group of the structure —N—R wherein R is any of an acyl, substituted acyl, alkyl, substituted alkyl, arylalkyl, alkenyl, alkynyl, aryl, heteroaryl, heterocyclic, acyl, cyano, alkoxy, aryloxy, heteroaryloxy or amido group. In some aspects a nucleotide may contain a cytosine base having a group covalently attached thereto, such that the C5 atom has attached a group of the structure —C—R wherein R is any of an acyl, substituted acyl, alkyl, substituted alkyl, arylalkyl, alkenyl, alkynyl, aryl, heteroaryl, heterocyclic, acyl, cyano, alkoxy, aryloxy, heteroaryloxy or amido group. In some aspects a nucleotide may contain a uracil base having a group covalently attached thereto, such that the C5 atom has attached a group of the structure —C—R wherein R is any of an acyl, substituted acyl, alkyl, substituted alkyl, arylalkyl, alkenyl, alkynyl, aryl, heteroaryl, heterocyclic, acyl, cyano, alkoxy, aryloxy, heteroaryloxy or amido group.

In one set of embodiments, these substrate nucleotides may serve as substrates for catalytic biomolecules. They may be modified and/or non-modified. For example, as catalytic biomolecules are being produced or provided in the microfluidic droplet and nucleotides with some specific chemical modification or modifications are mixed together in the compartment, the catalytic molecule may recognize such compound as a substrate and catalyze chemical conversion. To further exemplify, such catalyzed chemical conversion may be transformation of non-modified nucleotides into modified nucleotides, transformation of modified nucleotides into non-modified nucleotides, a chemical conversion that further modifies modified nucleotides or other. In another example, such chemical conversion may be oxido-reduction, transfer of a chemical group, hydrolysis, bond cleavage other than hydrolysis or oxidation, changes within a single molecule, joining two molecules with concomitant hydrolysis of the diphosphate bond in ATP or other.

In another set of embodiments, after catalytic biomolecule performs the chemical conversion of substrate nucleotide, nucleic acid synthesis may be initiated in at least some of the droplets. In some cases, this synthesized nucleic acid may be used to determine the amount of nucleotides that were converted and/or not converted by catalytic biomolecule by incorporating those nucleotides into DNA molecule during nucleic acid synthesis. In some cases, the nucleic acid synthesis reagents may be encapsulated into the droplets together with genetic information carriers. In other cases, the nucleic acid synthesis reagents may be introduced into droplets in later steps. For example, such introduction may be achieved using droplet merging techniques, wherein droplets with nucleic acid synthesis reagents are merged with droplets which may contain genetic information carriers, nucleotides and other. In some cases, the template for nucleic acid synthesis may be the same DNA template from which the catalytic biomolecule was produced in the droplet.

In one set of embodiments, the amplified DNA fragments in the droplet may contain specific amounts of reference nucleotides and modified substrate nucleotides. In some cases, these fragments may be sequenced and the information about specific catalytic biomolecule sequence and flanking genetic regulatory sequences may be retrieved. Also in some cases, besides the biomolecule's sequence, the substrate nucleotides, modified substrate nucleotides and reference nucleotides may also be registered in the sequenced fragments. For example, this may be achieved by using nanopore sequencing, bisulfite sequencing, tethered oligonucleotide-primed sequencing, PacBio sequencing or others. In some cases, this information about chemically converted nucleotides may be correlated with specific catalytic biomolecule activity. For example, in one particular droplet a specific catalytic biomolecule mutant may catalyze the chemical conversion of all of the substrate nucleotides, and in another droplet, a different catalytic biomolecule may only catalyze the chemical conversion of few substrate nucleotides. In last example, the first catalytic biomolecule may have a stronger catalytic activity then the second one. By that logic, billions of different catalytic biomolecules can have their catalytic activity recorded in DNA sequence. As this information is retrieved, it is possible to assign each catalytic biomolecule a sequence and its relative activity in that experiment.

In yet another set of embodiments, the substrate nucleotide may be incorporated into DNA during nucleic acid synthesis. In some cases, if the same mentioned substrate nucleotide is chemically converted into modified substrate nucleotide it may also be incorporated into DNA during nucleic acid synthesis. In those cases, the catalytic biomolecule activity and/or amount may be determined by comparing the amount of substrate nucleotide to reference nucleotide in the amplified DNA fragment.

In another set of embodiments, the substrate nucleotide may be incorporated into DNA during nucleic acid synthesis. In some cases, if the same mentioned substrate nucleotide is chemically converted into modified substrate nucleotide it may not be incorporated into DNA during nucleic acid synthesis. In those cases, the catalytic biomolecule activity and/or amount may be determined by comparing the amount of substrate nucleotide to reference nucleotide in the amplified DNA fragment.

In FIG. 1, an example of one aspect of the invention is provided. However, it should be understood that this is by way of example only; other examples and embodiments of the invention are discussed in further detail below. In the non-limiting example of FIG. 1, a population of genetic information carriers in the form of DNA molecules (10), encoding different mutants (11, 12, 13 . . . ) of the catalytic biomolecule desired to be analyzed. For example, such encoded catalytic biomolecule may be a protein, DNA, RNA or other molecules. Although purified DNA templates are used in this example as a source of nucleic acid material, this is by way of example, and in other embodiments, the nucleic acid may be introduced into the droplets from others sources or using other techniques. For example, genetic information carriers can be encapsulated in the form of RNA or cells.

The DNA templates may first be encapsulated in a series of microfluidic droplets (30). In some cases, the DNA molecules (or genetic information carriers in general) may be encapsulated at a density of no more than 1 molecule/droplet to ensure that most or all of the droplets have only zero or one molecule in them. Thus, as is shown in FIG. 1, each droplet (31, 32, 33, 34 . . . ) has either zero or one molecule present in them.

Also, encapsulated in the droplets, may be reagents for cell-free protein synthesis and substrate nucleotides (20). In other cases, cell-free protein expression reagents may not be necessary. For example, when using cells as genetic information carrier, cell lysis reagents may be encapsulated instead, together with cells that already contain a particular catalytic biomolecule. Substrate nucleotides (20) may be, for example, modified deoxyribonucleotide triphosphates-dATP and/or dCTP and/or dGTP and/or dTTP. The substrate nucleotides can be encapsulated together with DNA templates simultaneously or sequentially, in any suitable order. In one set of embodiments, modification of dNTPs may be chosen by the desired catalytic biomolecule reaction activity and its substrate, which may be the modification itself.

In some cases, four different substrate nucleotides may be used. In those cases, the four different substrate nucleotides may be different nucleotides (dATP, dCTP, dGTP, dTTP). In those cases, four different reference nucleotides (dATP, dCTP, dGTP, dTTP) may also be used. Depending on different situations, various combinations of different number of unique substrate and reference nucleotides may be used.

Droplets may then be incubated to produce catalytic biomolecules of interest by the previously encapsulated cell-free protein expression reagents. Produced biomolecules may (40, 41) or may not (42) have a catalytic activity required to catalyze a chemical conversion of modified nucleotides. In this example, chemical conversion may be a removal of chemical modifications from modified substrate nucleotides. In some cases, different catalytic biomolecule variants will have different activities on substrate nucleotides (20).

In FIG. 1, a specific catalytic biomolecule mutant (40) may remove the modifications from large amounts of substrate nucleotides (21), another mutant (41) may remove small amounts of modifications from substrate nucleotides (22) and the last mutant (42) may not be able to remove modifications from any of substrate nucleotides at all. In some cases, amount of substrate nucleotides which had their modifications removed may serve as a basis for biomolecule activity determination. For example, the droplet in which catalytic biomolecule (40) was produced, that biomolecule removed modifications from high number of substrate nucleotides and in turn may have a higher activity, compared to another droplet with different biomolecule (41) which removed modifications from lower number of substrate nucleotides.

In some cases, each droplet may be enriched with additional reagents-DNA amplification mix and reference nucleotides (50) which may have chemical modification. As shown later, reference nucleotides may be used to track the number of modified substrate nucleotides or/and not modified substrate nucleotides. The droplet enrichment, for example, can be achieved by droplet merging techniques. In some cases, reference nucleotides (60) may be chosen such that specific DNA polymerases may be able to incorporate them during nucleic acid synthesis reaction. In some cases, after the droplet enrichment, the catalytic biomolecule DNA templates (10, 11, 12 . . . ) may be amplified by polymerase mix (40).

In one set of embodiments, during the amplification of nucleic acid templates, both reference nucleotides (50) and modified substrate nucleotides (21) are incorporated in the synthesized DNA fragments (70, 71, 72). In this example, the DNA polymerase cannot incorporate substrate nucleotides into synthesized nucleic acid strand. In other cases, DNA polymerase can incorporate substrate nucleotides into synthesized nucleic acid strand.

In some cases, the amplification reaction may be an isothermal multiple displacement amplification (MDA) reaction which produces multiple long molecules with repeats of the same template. In some cases such amplification may also be performed by polymerase chain reaction. The resulting amplified DNA fragments (70, 71, 72 . . . ) incorporate reference nucleotides (60) and modified substrate nucleotides (21, 22) which are highlighted in those DNA sequences 80, 81, 82, respectively, to visualize the exemplary positions of those nucleotides. It should be understood that number, position of the nucleotides and their modifications may vary in different uses and examples.

It should also be understood that although FIG. 1 depicts substrate nucleotides (20) that are encapsulated into droplets (30), in other embodiments these nucleotides need not necessarily be encapsulated into these droplets. For example, substrate nucleotides (20) may be added during droplet enrichment.

Droplets (31, 32, 33, 34 . . . ) may then be "burst" or be "broken" to release their contents, and in some cases, the nucleic acids present in each droplet may be combined or pooled together, as is shown in FIG. 1. Each of the different catalytic biomolecule mutant's amplified DNA may have different amounts of reference nucleotides and/or modified substrate nucleotides and/or substrate nucleotides, which may consequently give the information about that biomolecule's activity. Accordingly, subsequent analysis (e.g. sequencing) of the combined pool of amplified or elongated nucleic acids may be performed and the substrate, modified substrate and reference nucleotides numbers may be resolved for each molecule. For example, information about catalytic biomolecule sequence and its activity may then be resolved using nanopore sequencing and/or bisulfite sequencing and/or tethered oligonucleotide-primed sequencing and/or PacBio sequencing which allows detecting DNA modifications.

The described example portraits a way to use substrate nucleotides as substrate for catalytic biomolecules and provides a series of steps that may be taken to record their catalytic activity. The amplified and resolved DNA may then provide information relating to all of the specific mutant sequences and relative catalytic activities of encoded biomolecules, in other words—the function-sequence relationship is recorded during the experiment. This method application example may be effortlessly expanded to characterize billions of different biocatalysts within the same experiment by simply preparing a larger library of mutants. Such large libraries can be created by using error-prone PCR, oligonucleotide-directed mutagenesis, assembly PCR, in vivo mutagenesis, cassette mutagenesis, recursive ensemble mutagenesis, exponential ensemble mutagenesis, site-specific mutagenesis or other techniques.

In another set of embodiments, all of the droplets may contain genetic information carriers that encode the same variant of catalytic biomolecule but have different genetic regulatory sequences. For example, such regulatory sequences can be ribosome binding sites (RBS), which are known to have different affinities for ribosomes depending on their sequences. In other cases, these regulatory sequences can be promoter sequence and/or ribozyme and/or riboswitch, transcription enhancer and/or operator and/or repressor binding site and/or activator binding site and/or DNA binding site and/or terminator and/or repressor encoding gene activator encoding gene. In such case, the amount of modified substrate nucleotides would not depend on catalytic biomolecule sequence, as they may all be the same in this example, but rather depend on genetic regulatory sequences which may affect the amount of the catalytic biomolecules produced. For example, if one genetic information carrier encodes an RBS sequence to which ribosomes bind with high affinity, there may be a lot more of catalytic biomolecule produced in that particular droplet and amount of modified substrate nucleotides would be larger. In some cases, using the invention, it may be possible to determine the RBS sequences and assign those sequences an activity value that would correlate with the ribosome binding affinity to that RBS sequence.

Figure 2:
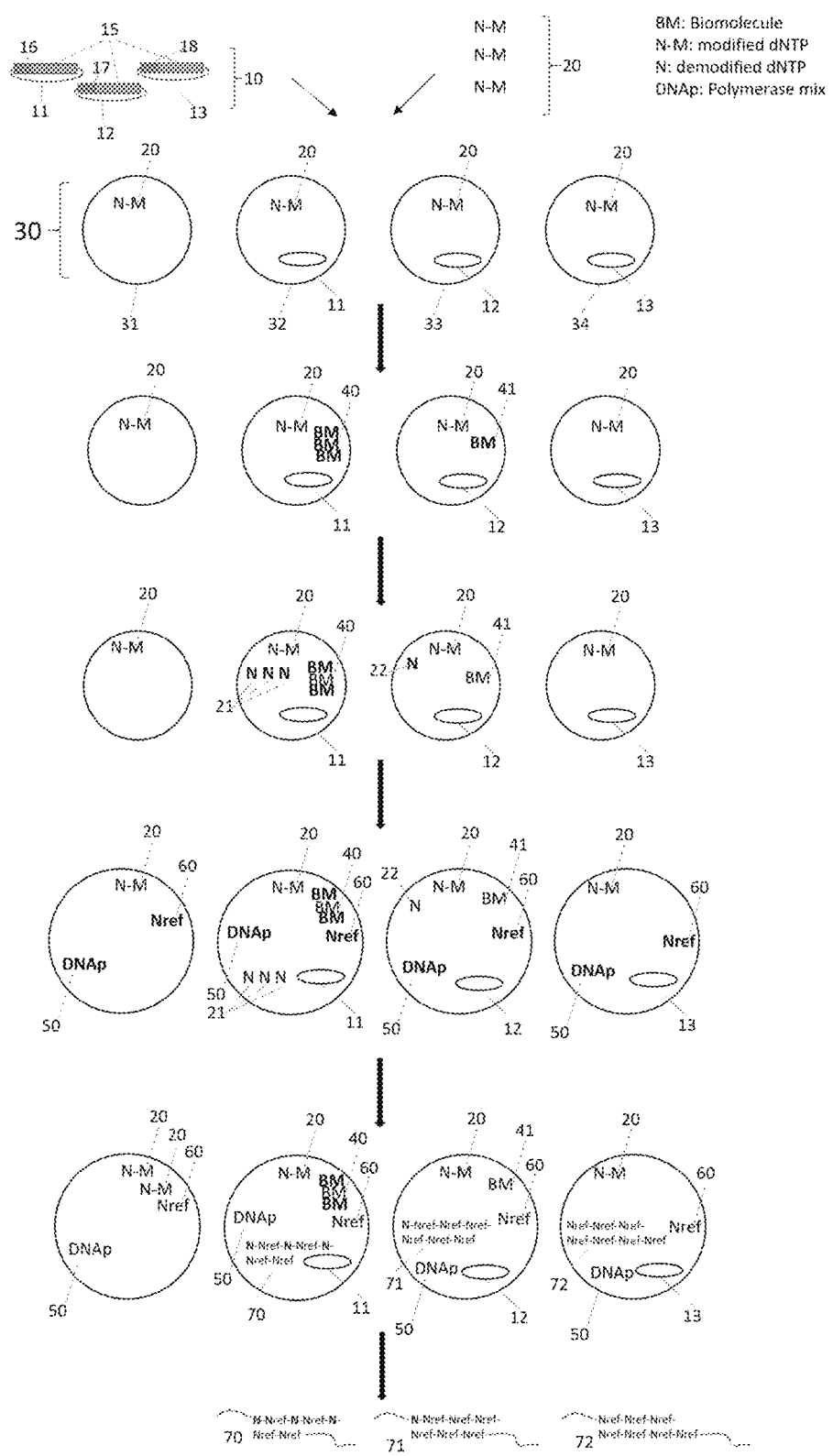
FIG. 2 illustrates a flowchart in accordance with another embodiment of the invention.

FIG. 2 is an example of another aspect of the invention which describes the modified substrate nucleotide amount adjustment by regulatory DNA sequences and how the information about different regulatory sequences and corresponding activities may be recorded and retrieved. In the non-limiting example of FIG. 2, a DNA template population (10) in which each population member (11, 12, 13 . . . ) encodes the same catalytic biomolecule (15) but have different regulatory sequences (16, 17, 18). These regulatory sequences may affect the amount of catalytic biomolecule expressed. For example, the regulatory sequence may be a ribosome binding sequence (RBS) and depending on that RBS sequence, ribosomes may bind to the RBS sequence more or less frequently. This binding frequency may correlate with the amount of catalytic biomolecule produced in the cell. For example, low ribosome binding frequency may result in low protein amounts. Although purified DNA templates are used in this example as a source of nucleic acid material, this is by way of example, and in other embodiments, the nucleic acid may be introduced into the droplets from others sources or using other techniques. For example, genetic information carriers may be encapsulated in the form of RNA or cells.

The DNA templates may first be encapsulated in a series of microfluidic droplets (30). In some cases, the DNA molecules (or genetic information carriers in general) may be encapsulated at a density of less than 1 molecule/droplet to ensure that most or all of the droplets have only zero or one molecule in them. Thus, as is shown in FIG. 2, each droplet (31, 32, 33, 34 . . . ) has either zero or one molecule present in them.

Also, encapsulated in the droplets, may be reagents for cell-free protein synthesis and substrate nucleotides (20). In other cases, cell-free protein expression reagents may not be necessary. For example, when using cells as genetic information carrier, cell lysis reagents can be encapsulated together with cells. In that case, cells may be lysed in the droplet, which release their cellular content inside the droplet, which may contain catalytic biomolecules produced in the cell and their DNA templates. Substrate nucleotides (20) may be, for example, modified deoxyribonucleotide triphosphates-dATP and/or dCTP and/or dGTP and/or dTTP. The substrate nucleotides can be encapsulated together with DNA templates simultaneously or sequentially, in any suitable order.

Droplets may then be incubated to produce catalytic biomolecules using the previously encapsulated cell-free protein expression reagents. In some cases, DNA template molecules sharing the same coding sequences will express different amount of catalytic biomolecules due to different regulatory sequences. In this example, those regulatory sequences are different ribosome binding sites. In this illustrative example, first DNA template (11) may produce the most catalytic biomolecules (40), another DNA template (12) may produce less biomolecules (41) and last DNA template (13) may produce no biomolecules.

The produced catalytic biomolecules in each droplet may then start catalyzing chemical conversion of the substrate nucleotides. As every DNA template encodes the identical catalytic biomolecule, the activity of each biomolecule is the same, and the overall chemical conversion amount may only depend on the biomolecule's concentration in the droplet. In this example, droplet (32) contains the most catalytic biomolecules (40) and consequently they may produce more modified substrate nucleotides then another droplet (33) with lower amounts of catalytic biomolecules (41). In some cases, different catalytic biomolecule concentrations between droplets may give information about different activity of regulatory sequences-decreasing catalytic biomolecule amounts from droplet (32) to droplet (33) may show how ribosomes may have different affinities for different RBS sequences. For example, template (11) may have a specific RBS sequence that strongly increases the frequency of ribosome binding to that RBS sequence for protein synthesis initiation, while (12) and (13) may have RBS sequence variants that have a lesser effect on ribosome binding frequency.

In some cases, each droplet may be enriched with additional reagents-DNA amplification mix (50) and reference nucleotides (60). As shown later, reference nucleotides may be used to track the number of substrate nucleotides and/or modified substrate nucleotides. The droplet enrichment, for example, can be achieved by droplet merging techniques. In some cases, reference nucleotides (60) may be chosen such that specific DNA polymerases may be able to incorporate them during nucleic acid synthesis. In other cases, reference nucleotides (60) may be chosen such that specific DNA polymerases may not be able to incorporate them during nucleic acid synthesis. In some cases, after the droplet enrichment, the initial biomolecule templates (11, 12, 13 . . . ) may be amplified by polymerase mix (50).

In one set of embodiments, during the amplification of templates, reference nucleotides (60) and modified substrate nucleotides (21, 22 . . . ) are incorporated in the amplified DNA fragments (70, 71, 72). In this example, the DNA polymerase cannot use the substrate nucleotides as substrates for DNA amplification. In some cases, DNA polymerase may use the substrate nucleotides as substrates for DNA amplification. In this example, the amplification reaction may be an isothermal multiple displacement amplification (MDA) reaction which results in multiple long nucleic acid molecules with repeats of the same template. In some cases, such amplification may also be completed by polymerase chain reaction. The resulting amplified DNA fragments (70, 71, 72 . . . ) may incorporate reference nucleotides (60) and/or modified substrate nucleotides (21, 22 . . . ) and/or substrate nucleotides. It should be understood that number, position of the substrate nucleotides in DNA amplicon and the type of substrate, modified substrate and reference nucleotides may vary in different uses and examples.

It should also be understood that although FIG. 2 depicts substrate nucleotides (20) that are encapsulated into droplets (30), in other embodiments, these nucleotides need not necessarily be encapsulated into these droplets. For example, substrate nucleotides (20) can be added during already described droplet enrichment process.

Droplets (31, 32, 33, 34 . . . ) may then be "burst" or be "broken" for the same effects as in FIG. 1. Each different amplified DNA sequence may have different amounts of reference nucleotides and/or modified substrate nucleotides and/or substrate nucleotides in their sequence. The nucleotide amounts may consequently give the information about that regulatory sequence activity, which in this case are the different ribosome affinities to different RBS sequences. Accordingly, subsequent analysis (e.g. sequencing) of the combined pool of amplified or elongated nucleic acids may be performed and the specific amounts of reference nucleotides and/or modified substrate nucleotides and/or substrate nucleotides may be resolved for each molecule. For example, nucleotide amount may be resolved using nanopore sequencing or other sequencing methods which allow detecting DNA modifications.

The described example portrays a way to use substrate nucleotides as a target for catalytic biomolecules and then provides a series of steps that may be taken record catalytic biomolecule activity. In this example, the amount of modified substrate nucleotides produced was not based on different catalytic biomolecule activities, but instead, on their regulatory sequences which altered the amount of catalytic biomolecules produced in each droplet. The amplified DNA may then be resolved and then may provide the information about every different regulatory sequence and its relative activity. In other words, the function and sequence relationship is recorded for regulatory sequences is recorded.

This method application example may be effortlessly expanded to characterize billions different regulatory sequence variants within the same experiment by simply preparing a larger library of mutants. Such large libraries can be created by using error-prone PCR, oligonucleotide-directed mutagenesis, assembly PCR, in vivo mutagenesis, cassette mutagenesis, recursive ensemble mutagenesis, exponential ensemble mutagenesis, site-specific mutagenesis or other techniques.

Sequencing

In some aspects, the methods disclosed herein further comprise determining the sequence of the library-molecule or any product thereof. Determining the sequence of the genetic information carrier or any product thereof can be performed by sequencing methods such as Helioscope™ single molecule sequencing, Bisulfite sequencing, Tethered Oligonucleotide-Primed sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLID sequencing, Ion Torrent™, Ion semiconductor sequencing, Single Molecule SMRT sequencing, Polony sequencing, DNA nanoball sequencing, and VisiGen Biotechnologies approach. Alternatively, determining the sequence of the DNA molecule or any product thereof can use sequencing platforms, including, but not limited to, Genome Analyzer IIx, HiSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, MA).

In some instances, determining the sequence of the nucleic acid molecule or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the nucleic acid molecule or any product thereof can be determined by electron microscopy or a chemical-sensitive field effect transistor (chemFET) array.

In another example, determining the sequence of the mutant or any product thereof comprises RNA-Seq or microRNA sequencing. Alternatively, determining the sequence of labeled-molecules or any products thereof comprises protein sequencing techniques such as Edman degradation, peptide mass fingerprinting, mass spectrometry, or protease digestion.

The sequencing reaction can, in certain embodiments, occur on a solid or semi-solid support, in a gel, in an emulsion, on a surface, on a bead, in a drop, in a continuous follow, in a dilution, or in one or more physically separate volumes.

Sequencing may comprise sequencing at least about 10, 20, 30, 40, 50, 60, 70, 80, 90, 100 or more nucleotides or base pairs of the labeled molecule. In some instances, sequencing comprises sequencing at least about 200, 300, 400, 500, 600, 700, 800, 900, 1000 or more nucleotides or base pairs of the labeled molecule. In other instances, sequencing comprises sequencing at least about 1500; 2,000; 3,000; 4,000; 5,000; 6,000; 7,000; 8,000; 9,000; or 10,000 or more nucleotides or base pairs of the labeled molecule.

Sequencing may comprise at least about 200, 300, 400, 500, 600, 700, 800, 900, 1000 or more sequencing reads per run. In some instances, sequencing comprises sequencing at least about 1500; 2,000; 3,000; 4,000; 5,000; 6,000; 7,000; 8,000; 9,000; or 10,000 or more sequencing reads per run.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Hereafter, the present invention is described in greater detail with reference to the examples, although the technical scope of the present invention is not limited to the following examples.

Example 1

This example illustrates how the activities of different catalytic biomolecules can be measured and recorded to corresponding biomolecule DNA templates by amplification and then retrieved by sequencing techniques.

In this case a library of esterase enzyme mutants were prepared using error-prone PCR that may have the ability to catalyze a conversion of substrate nucleotides (N4-benzoyl-2'-deoxycytidine triphosphates) to modified substrate nucleotides (2'-deoxycytidine triphosphate). Also, in this example, the esterase mutants were expressed using an in vitro (cell-free) transcription and translation system.

Figure 3:
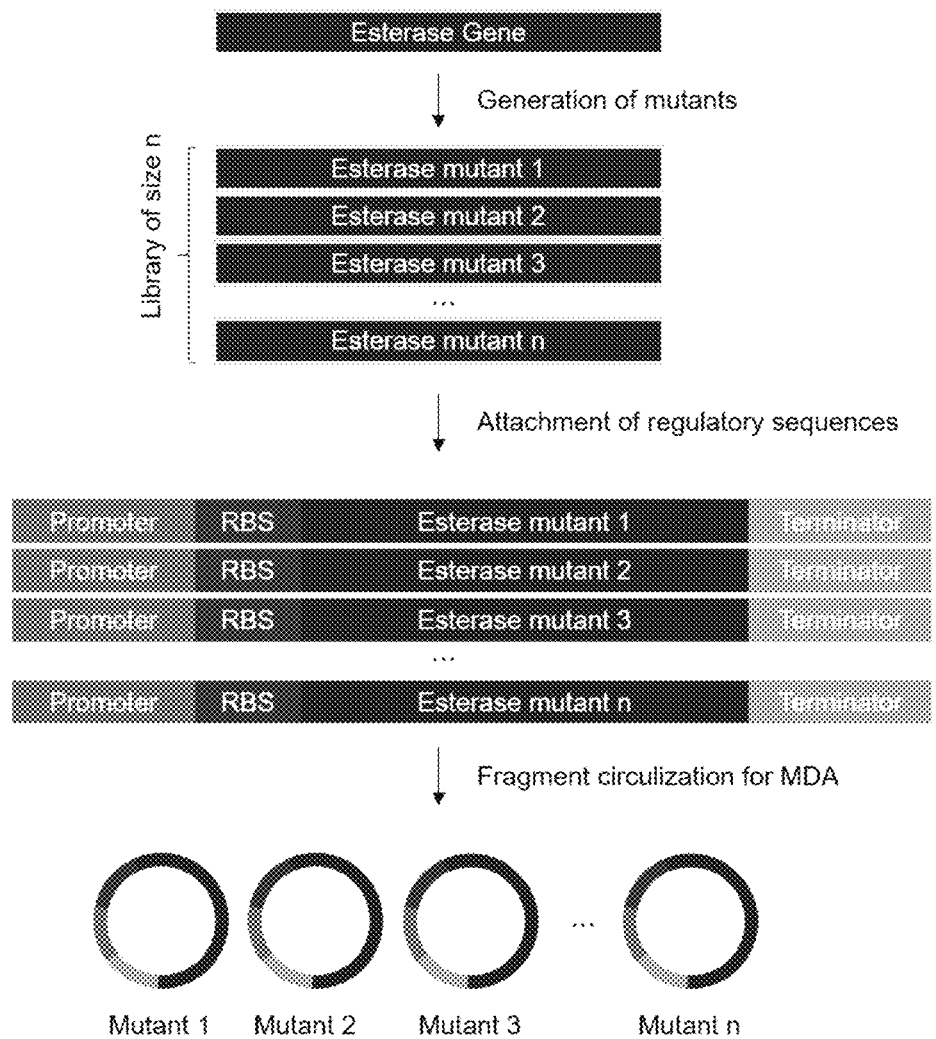
FIG. 3 illustrates a flowchart for catalytic biomolecule mutant library preparation used in some of the embodiments of the invention.
Figure 4:
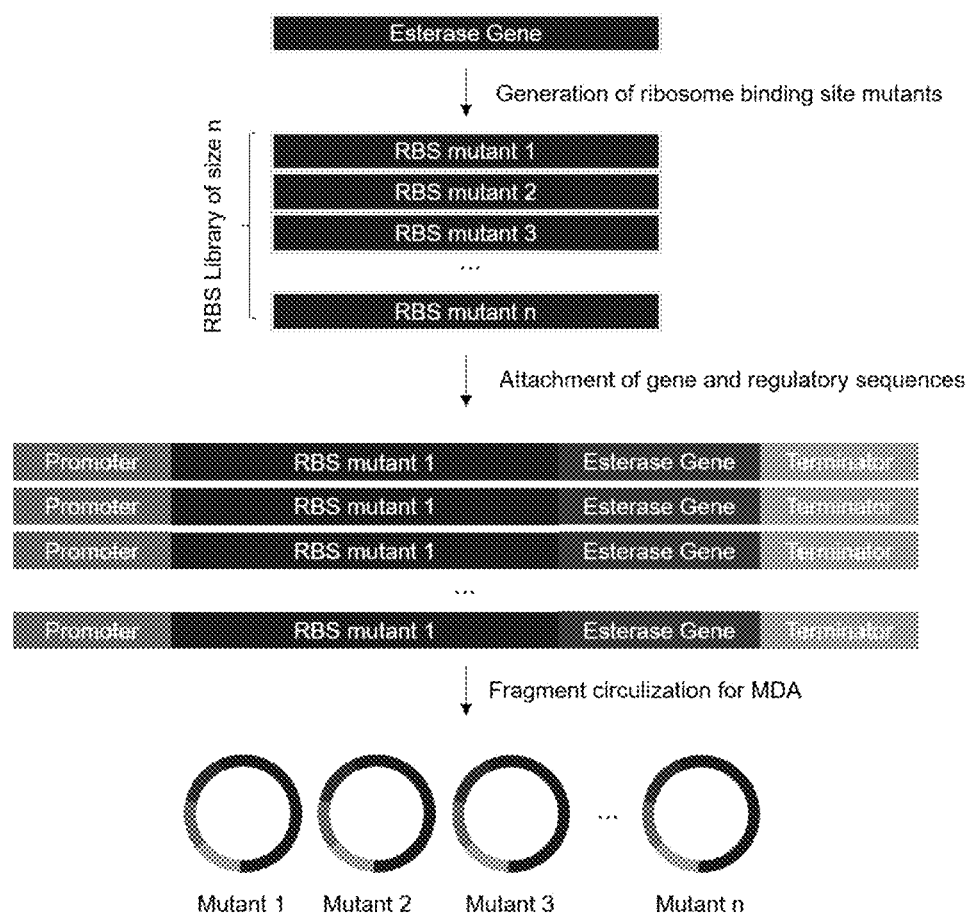
FIG. 4 illustrates a flowchart for genetic regulatory sequence mutant library preparation used in some of the embodiments of the invention.

As illustrated in FIG. 3, a DNA library is prepared by synthesizing different mutants of an esterase enzyme by well-known mutagenesis techniques (e.g. error-prone PCR) and then attaching regulatory DNA sequences that are required in order to express catalytic biomolecules in cell-free environment—a promoter, ribosome binding site (RBS) and a terminator. The linear DNA fragments were circularized, because in this example multiple displacement amplification, which requires a circular DNA template.

First, two 1 mL syringes are mounted with 0.351 mm diameter needles and 0.3 mm diameter polytetrafluoroethylene tubings. The first syringe is then filled with 200 μL 1.5% EA surfactant in HFE7500 fluorinated oil (v/v). The second syringe is filled with 300 μL HFE7500 fluorinated oil.

Next, In Vitro Transcription and Translation (IVTT) (PURExpress® In Vitro Protein Synthesis Kit) reaction mix is prepared according to Table 1 and placed on ice.

TABLE 1

In vitro transcription and translation reaction mix

| | Initial concentration | Final concentration | Volume to add |
|---|---|---|---|
| Esterase biomolecule library | ~20000 molecules/μL | ~10000 molecules/μL | 1.5 μL |
| PURexpress Solution A | 3X | 1X | 10 μL |
| PURexpress Solution B | 4X | 1X | 7.5 μL |
| Ribolock RNase inhibitor | 40 U/μL | 1.33 U/μL | 1 μL |
| Substrate nucleotides | 1 mM | 0.125 mM | 3.75 μL |
| H$_2$O | | | 6.25 μL |

Then the prepared IVTT reaction mix is transferred to the second syringe prefilled with HFE7500 which is then kept in a vertical position for the rest of the experiment. The syringes are then primed (fluid reaches the end of the tubing) by precision flow control pumps. It is mandatory to keep the syringes as close to 4° C. as possible in order to avoid premature reactions. For example one may use a cooling jacket on the syringe to keep the reaction mix cold.

Microfluidic droplet generation device is placed under the microscope. Tubing of the first syringe is then inserted in outer carrier oil phase inlet of the device. The tubing of second syringe is inserted into the water phase inlet. Then with the use of pumps both syringes are slowly pushed until both fluids reach the device channels.

The infusion speed of both syringes is then set to 300 μL/h for carrier oil syringe and 250 μL/h for the water syringe in order to produce water droplets with volume around 10 pL±1 pL. When the production of droplets stabilizes, the formed emulsion is collected with 0.56 mm tubing placed into the outlet of the device. The tubing with collected emulsion is kept cold using an ice jacket.

While the droplets are being formed, a third syringe is prepared by attaching a 0.58 mm needle and filling it with 500 μL HFE7500 fluorinated oil. The syringe is then mounted into the precision flow control pump vertically. After the water phase is exceeded and droplet forming is diminished, the infusion of fluorinated oil is continued for another 3 minutes.

Then, the third needle which does not have a tubing is infused at a rate of 500 μL/h. Then, the outlet tubing is quickly removed and placed on the third needle. The other end of the tubbing is wrapped with plastic paraffin film to avoid contact with air. The sealed tubing with emulsion is then placed in 37° C. thermostat together with the mounted syringe for 4 hours.

During the incubation at 37° C. the esterase enzyme mutants are produced in each droplet. As they are being synthesized some mutants may start to catalyze chemical conversion of the substrate nucleotides. Modified substrate nucleotide concentration is then established in each droplet. The number of modified substrate nucleotides may depend on the activity of specific esterase mutant in droplets.

After the incubation the experiment is continued by preparing three 1 mL syringes mounted with 0.58 mm diameter needles with 0.56 mm diameter polytetrafluoroethylene tubing. First and second syringes are filled with 300 μL 1.5EA surfactant in HFE7500 fluorinated oil (v/v). The third syringe is filled with 300 μL HFE7500 fluorinated oil.

For this experiment reference nucleotides were to be 2'-deoxy-5-methylcytidine 5'-triphosphates. Phi29 polymerase can successfully incorporate them into the DNA strand during the nucleic acid synthesis.

Multiple displacement amplification (MDA) reaction mixture is then prepared according to Table 2.

TABLE 2

Multiple displacement amplification (MDA) reaction mixture

| | Initial concentration | Final concentration | Volume to add |
|---|---|---|---|
| 10X Phi29 reaction buffer | 10X | 1.25X | 12.5 μL |
| Exo-resistant random hexamers | 500 μM | 10 μM | 2 μL |
| dATP, dGTP, dTTP and 2'-deoxy-5-methylcytidine 5'-triphosphate | 10 mM | 0.375 mM | 3.75 μL |
| Pluronic F-127 | 10% | 1.25% | 12.5 μL |
| Pyrophosphatase | 0.1 U/μL | 0.00125 U/μL | 1.25 μL |
| Phi29 polymerase | 10 U/μL | 0.67 U/μL | 6.7 μL |
| DTT | 100 mM | 2.5 mM | 2.5 μL |
| Water | | | 53.3 μL |

The prepared MDA reaction mixture is then transferred to the third syringe. Fluids in all the three syringes are pushed out into the tubing by gently pressing the valve on the bottom and later placed into precision flow control pumps. The MDA reaction syringe must be placed vertically. Also, an ice jacket is required on the third syringe mounted in the pumps to make sure the reaction does not start before encapsulation.

The previously incubated IVTT reaction syringe is then taken out of the thermostat. The emulsion in the tubing is pushed until it reaches the end of the tubing.

The 30 μm droplet merging device with Bi—Sn alloy electrodes is placed onto the microscopic table and high voltage cables are attached to the electrodes. The ends of the tubings are inserted to device inlets. Electrical impulse generator is then connected to high voltage source.

The tubing with previously incubated IVTT reaction together with its syringe is mounted into the precision flow control pump which is placed at a lower height than the microfluidic droplet merging device. The tubing with IVTT emulsion is inserted into the emulsion reinfusion inlet. A fresh 0.56 mm tubing without a needle is inserted into outlet of the device.

The MDA reaction mixture infusion is then initiated with flow rates of 100 μL/h for water phase and 270 μL/h for carrier oil in order to make 40 μL droplets.

Reinjected IVTT 10 μL droplets are infused at rates 30 μL/h for droplets and 300 μL/h for carrier oil.

The flow rates may be different in different experiments depending on voltage used with merging device, the initial IVTT droplet volume, surfactant used and other parameters.

The freshly formed MDA and reinjected IVTT droplets are merged by applying square waveform current with 10 KHz frequency, 300-700 mVpp amplitude. The merging is continued until all of the IVTT droplets are infused and merged. The collected emulsion is placed in 30° C. for 5 hours to perform MDA reaction and then at 65° C. for 20 minutes to inactivate the polymerase.

After the IVTT reaction droplets had different amounts of modified substrate nucleotides. The amount of modified substrate nucleotides was based on the activity of different esterase mutants in each droplet. Droplets that were merged with the droplets with modified substrate nucleotides contained the identical amount of reference nucleotides (2'-deoxy-5-methylcytidine 5'-triphosphate) in each droplet. Merged droplets then may contain a specific substrate nucleotide and reference nucleotide ratio.

As multiple displacement amplification reaction begins, the specific amount of modified substrate and reference nucleotides were incorporated into the DNA amplicon. Hence, in every droplet the DNA amplicon then may contain different amounts of modified substrate and reference nucleotides. DNA templates used for DNA amplification in different droplets are the same circular DNA templates from which catalytic biomolecules were produced.

After the MDA reaction and MDA reaction inactivation steps are over, the emulsion can be broken by adding equal volume of 1H,1H,2H,2H-Perfluoro-1-octanol (Pfo). The water phase is then cleaned with Ampure XP beads using bead ratio of 0.4 to water phase volume. After purification steps DNA is sequenced by nanopore technique using manufacturer's protocols. In this case, Nanopore sequencing was chosen because of its ability to read long DNA molecules (the need for fragmentation and barcoding is eliminated) and also its ability to detect nucleotide modifications.

The sequencing data reveals plurality of details. First of all, it provides the information about the mutant sequences of the initially prepared DNA library. Secondly, at the same time of retrieving mutant sequence some of the nanopore post-processing algorithms (for example, "SignalAlign" or "Nanomod" algorithms) may detect nucleotide modifications in the recorded signal. As mentioned earlier, the amplified DNA in each droplet contains a different amount of modified substrate and reference nucleotides. As some nanopore algorithms can detect nucleotide modifications, it enables accurate quantification of those nucleotides for each molecule. As the modified substrate nucleotide concentration in each droplet depends on the activity of the particular esterase mutant, the increased ratio of modified substrate nucleotide to reference nucleotide indicates increased enzymatic activity of a specific esterase mutant, and the decreased ratio indicates a decreased activity of the esterase mutant.

Figure 5:
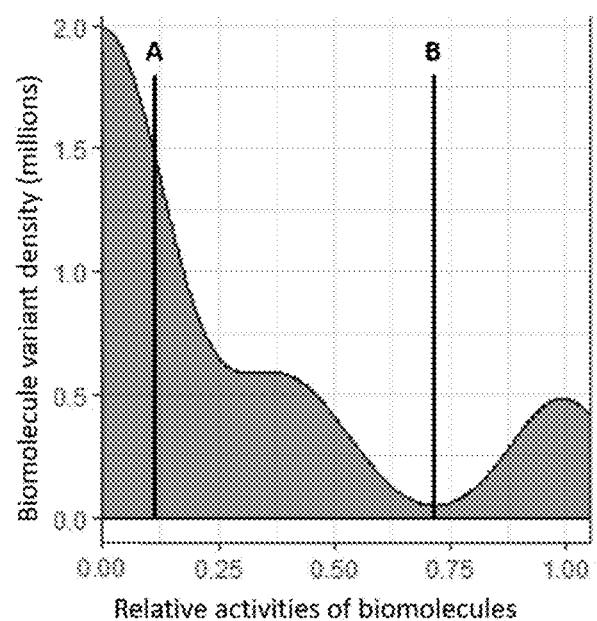
FIG. 5 illustrates a diagram in accordance with results of one embodiment of the invention.

How such results may look is illustrated in FIG. 5, where Y axis shows the number of unique mutants (biomolecule variants) and X axis describes the relative activity distribution. It should be noted that even though the figure illustrates a distribution by density, each unique mutant sequence has a specific known sequence. For example, marked on the figure as A and B are two different esterase mutant DNA sequences. After the experiment both sequence and the activity is known for those mutants. Table 3 shows the relative recorded activities of A and B mutants and their DNA sequences.

TABLE 3

Esterase mutant activities and their sequences recorded using the invention.

| Mutant variant | Relative Activities | DNA sequence |
| --- | --- | --- |
| A | 0.115 | SEQ ID NO:1<br>ATGAGCTCACTTTTTATTGGGCAAGTATTCG<br>CGAAGACTCCCGAAGTACAAACCTCCGACTT<br>GACAGGTAACACCACCTGCTCGAACTTGGTT<br>GGAATGGTCATCCCGGCCGACGAGATCGGGC<br>TTCCTACATCAGGGGCTACAATCACATCAGC<br>GACCCTTAAAATCGTTGAAGATGGGGCTATC<br>AAAGACGCCGAATACTGTGAAGTGTTGGGAG<br>CGATTCACCCAGTCGATCCAACGGCGCCTGA<br>CATCAACTTTCAAGTGAACCTGCCAACAAAT<br>TGGAACAAAAGTTCTTACAGTTTGGCGGAG<br>GATATTTCAATGGCACCGTCCGCACAGGGCT<br>TGGAAATCCTCCTGCCGGCGACCGTAAGCTG<br>GGTAAGAACACCCCCTTGGCACAAGGGTATG<br>TGACCTTCGGGTCAGACAGTGGTAATAGTAC<br>CGCTCCGTTGGATGCATCTTTTGGTATGAAC<br>GACGAGGCATTAAAAAATTTCGCGGGAGATC<br>AGCTGAAAAAGACTAAGGATGTAGCTTTAGC<br>CTTGGCTAACGTCCGTTATAATGCCGTACCG<br>GATCAAGTTTACTTCGCTGGAGGCTCCGAGG<br>GCGGTCGTGAGGGGTTGTTCATCGTCCAGAA<br>TTTTCCCGACGAGTACGATGGAGTCATTAGC<br>GTATACCCCGTATTAAACTGGATCCCCGTG<br>CTCTGAAGGATAACCGCGATGCTCAAGCACT<br>TTACAAGAATGACGGAGAGGGATGGATCTCC<br>CCAGAGGAGAACGACCTTATCAACGAGACTG<br>TATTCAAGGCATGCGATTCATTGGATGGCGT<br>AAAGGACGGTATTATTAGCAATACAAGTGAA<br>TGTGCCGAGAAAGAAGACAAAATTTTGGATA<br>CGTTAAGCGAGTCCCTGTCCGAGAAACAGAT<br>CGAGGTTATTAAGAGCTTTAACGGGCCAATG<br>GAGTTTGATATCCAGCTTGCCAACGATTTTA<br>CGACAATGCCTGGTTACTCACAGCTTCAGGG<br>TGCCGATATTGGTCGTTTGTTTGGTACTCGC |

TABLE 3-continued

Esterase mutant activities and their sequences recorded using the invention.

| Mutant variant | Relative Activities | DNA sequence |
| --- | --- | --- |
| | | TGACCTTCGGGTCAGACAGTGGTAATAGTAC<br>CGCTCCGTTGGATGCATCTTTTGGTATGAAC<br>GACGAGGCATTAAAAAATTTCGCGGGAGATC<br>AGCTGAAAAAGACTAAGGATGTAGCTTTAGC<br>CTTGGCTAACGTCCGTTATAATGCCGTACCG<br>GATCAAGTTTACTTCGCTGGAGGCTCCGAGG<br>GCGGTCGTGAGGGGTTGTTCATCGTCCAGAA<br>TTTTCCCGACGAGTACGATGGAGTCATTAGC<br>GTATACCCCGTATTAAACTGGATCCCCGTG<br>CTCTGAAGGATAACCGCGATGCTCAAGCACT<br>TTACAAGAATGACGGAGAGGGATGGATCTCC<br>CCAGAGGAGAACGACCTTATCAACGAGACTG<br>TATTCAAGGCATGCGATTCATTGGATGGCGT<br>AAAGGACGGTATTATTAGCAATACAAGTGAA<br>TGTGCCGAGAAAGAAGACAAAATTTTGGATA<br>CGTTAAGCGAGTCCCTGTCCGAGAAACAGAT<br>CGAGGTTATTAAGAGCTTTAACGGGCCAATG<br>GAGTTTGATATCCAGCTTGCCAACGATTTTA<br>CGACAATGCCTGGTTACTCACAGCTTCAGGG<br>TGCCGATATTGGTCGTTTGTTTGGTACTCGC<br>CCAATCCCTGGGGTGCCCCCCGTCGTGAGTG<br>AATCGGTCGGACACGTAATCGACGAGCAGGA<br>CGCTTTAATGGGCGTCTACAGTGATCAGGTG<br>ATCCGTTATAAGATCACGCGCAACCCAGACT<br>TCAATACTCTTACCTTCGACCCTAACGAGTA<br>CCGTGAAGAAATCTTAAAGGCTTCAAACCTG<br>CTGGACGTCACAGACCCTAATATCAGTGAAT<br>TTCGTGAGAATGGGGGGAAGCTGATTTTGGT<br>GCATGGCACCGAGGATGAAATGGTTGCACCA<br>CAAGGTACGAGTGACTATTATAGTAAACTGG<br>TCAATGAGTTCGGCCAAGAATCCTTGGACGA<br>GTTTGCACAGTACTACTTAGTACCTGGCTTC<br>TCACACGGTGGTGGTAACTTTACAATGTCTG<br>CAAATTTGTTGGGGGCCTTGGACGCCTGGGT<br>GGTAAATGGGGATGTACCTTCCAACTTGGTG<br>GCGGAAGATCAGAACTCGGCGACTTTCGGGC<br>GTACTCGTCCGTTGTGTGAATACCCTACATA<br>TCCCCAGTACAATGGGAGTGGCGACGTAAAT<br>TCTGCGGCCAGTTTTACATGCTTAAAAGCA |
| B | 0.75 | SEQ ID NO: 2<br>ATGAGCTCACTTTTTATTGGGCAAGTATTCG<br>CGAAGACTCCCGAAGTACAAACCTCCGACTT<br>GACAGGTAACACCACCTGCTCGAACTTGTT<br>GGAATGGTCATCCCGGCCGACGAGATCGGGC<br>TTCCTACATCAGGGGCTACAATCACATCAGC<br>GACCCTTAAAATCGTTGAAGATGGGGCTATC<br>AAAGACGCCGAATACTGTGAAGTGTTGGGAG<br>CGATTCACCCAGTCGATCCAACGGCGCCTGA<br>CATCAACTTTCAAGTGAACCTGCCAACAAAT<br>TGGAACAAAAGTTCTTACAGTTTGGCGGAG<br>GATATTTCGATGGCACCGTCCGCACAGGGCT<br>TGGAAATCCTCCTGCCGGCGACCGTAAGCTG<br>GGTAAGAACACCCCCTTGGCACAAGGGTATG<br>TGACCTTCGGGTCAGACAGTGGTAATAGTAC<br>CGCTCCGTTGGATGCATCTTTTGGTATGAAC<br>GACGAGGCATTAAAAAATTTCGCGGGAGATC<br>AGCTGAAAAAGACTAAGGATGTAGCTTTAGC<br>CTTGGCTAACGTCCGTTATAATGCCGTACCG<br>GATCAAGTTTACTTCGCTGGAGGCTCCGAGG<br>GCGGTCGTGAGGGGTTGTTCATCGTCCAGAA<br>TTTTCCCGACGAGTACGATGGAGTCATTAGC<br>GTATACCCCGTATTAAACTGGATCCCCAAGG<br>CTCTGAAGGATAACCGCGATGCTCAAGCACT<br>TTACAAGAATGACGGAGAGGGATGGATCTCC<br>CCAGAGGAGAACGACCTTATCAACGAGACTG<br>TATTCAAGGCATGCGATTCATTGGATGGCGT<br>AAAGGACGGTATTATTAGCAATACAAGTGAA<br>TGTGCCGAGAAAGAAGACAAAATTTTGGATA<br>CGTTAAGCGAGTCCCTGTCCGAGAAACAGAT<br>CGAGGTTATTAAGAGCTTTAACGGGCCAATG<br>GAGTTTGATATCCAGCTTGCCAACGATTTTA<br>CGACAATGCCTGGTTACTCACAGCTTCAGGG<br>TGCCGATATTGGTCGTTTGTTTGGTACTCGC |

TABLE 3-continued

Esterase mutant activities and their sequences recorded using the invention.

| Mutant variant | Relative Activities | DNA sequence |
|---|---|---|
| | | CCAATCCCTGGGGTGCCCCCCGTCGTGAGTG
AATCGGTCGGACACGTAATCGACGAGCAGGA
CGCTTTAATGGGCGTCTACAGTGATCAGGTG
ATCCGTTATAAGATCACGCGCAACCCAGACT
TCAATACTCTTACCTTCGACCCTAACGAGTA
CCGTGAAGAAATCTTAAAGGCTTCAAACCTG
CTGGACGTCACAGACCCTAATATCAGTGAAT
TTCGTGAGAATGGGGGAAGCTGATTTTGGT
GCATGGCACCGAGGATGAAATGGTTGCACCA
CAAGGTACGAGTGACTATTATAGTAAACTGG
TCAATGAGTTCGGCCAAGAATCCTTGGACGA
GTTTGCACAGTACTACTTAGTACCTGGCTTC
TCACACGGTGGTGGTAACTTTACAATGTCTG
CAAATTTGTTGGGGGCCTTGGACGCCTGGGT
GGTAAATGGGGATGTACCTTCCAACTTGGTG
GCGGAAGATCAGAACTCGGCGACTTTCGGGC
GTACTCGTCCGTTGTGTGAATACCCTACATA
TCCCCAGTACAATGGGAGTGGCGACGTAAAT
TCTGCGGCCAGTTTTACATGCTTAAAAGCA |

In this way, using this invention, millions to billions (or more) of unique mutant sequences and their activities can be recorded and retrieved.

Example 2

This example makes use of substrate nucleotides (N4-benzoyl-2'-deoxycytidine triphosphates) and an esterase enzyme that can catalyze chemical conversion of those substrate nucleotides and in turn produce modified substrate nucleotides (2'-deoxycytidine triphosphates). It should be noted that this specific substrate nucleotide was only used as an example, and other types of substrate nucleotides may be used with the same or similar experimental workflow as described in this example and this is also true for the choice of catalytic biomolecule. Also, in this example, the catalytic biomolecules were expressed using an in vitro transcription and translation system.

The goal of this example is to illustrate that this invention can be applied not only for catalytic biomolecule activity determination but also for genetic regulatory sequence characterization as ribosome binding site (RBS) or other. It is known that frequency of ribosome binding to RBS is RBS sequence dependent, and some sequences of RBS may increase this binding, while some-decrease it. In other words, this is a step by step example of how the invention can be applied to multiple regulatory part activity characterization.

As illustrated in FIG. 3, a DNA library is prepared by synthesizing different mutants of an esterase enzyme by well-known mutagenesis techniques (e.g. error-prone PCR) and then attaching regulatory DNA sequences that are required in order to express catalytic biomolecules in cell-free environment—a promoter, ribosome binding site (RBS) and a terminator. The linear DNA fragments were circularized, because in this example multiple displacement amplification, which requires a circular DNA template.

First, two 1 mL syringes are mounted with 0.351 mm diameter needle and 0.3 mm diameter polytetrafluoroethylene tubing. The first syringe is then filled with 200 μL 1.5% EA surfactant in HFE7500 fluorinated oil (v/v). Then the second syringe is filled with 300 μL HFE7500 fluorinated oil.

Next, In Vitro Transcription and Translation (IVTT) (PURExpress® In Vitro Protein Synthesis Kit) reaction mix is prepared according to Table 1, except that a "Ribosome binding site sequence library with a single esterase enzyme" is used instead of "Esterase biomolecule library", and placed on ice.

Then the prepared IVTT reaction mix is transferred to the second syringe prefilled with HFE7500 which is then kept in a vertical position for the rest of the experiment. The syringes are then primed (fluid reaches the end of the tubing) by precision flow control pumps. It is mandatory to keep the syringes as close to 4° C. as possible in order to avoid premature reactions. For example one may use a cooling jacket on the syringe to keep the reaction mix cold.

Microfluidic droplet generation device is placed under the microscope. Tubing of the first syringe is then inserted in outer carrier oil phase inlet of the device. The tubing of second syringe is inserted into the water phase inlet. Then, using pumps both syringes are slowly pushed until both fluids reaches the device channels.

The infusion speed of both syringes is then set to 300 μL/h for carrier oil syringe and 250 μL/h for the water syringe in order to produce water droplets with volume around 10 pL±1 pL. When the production of droplet stabilizes, the formed emulsion is collected with 0.56 mm tubing placed into the outlet of the device. The tubing with collected emulsion is kept cold using an ice jacket.

While the droplets are forming a third syringe is prepared by attaching a 0.58 mm needle and filling it with 500 μL HFE7500 fluorinated oil. The syringe is then mounted into the precision flow control pump vertically. After the water phase ends and droplet forming is diminished, the infusion of fluorinated oil is continued for another 3 minutes.

Then, the third needle which does not have a tubing is infused at a rate of 500 μL/h. Then, the outlet tubing is quickly removed and placed on the third needle. The other end of the tubing is wrapped with plastic paraffin film to avoid contact with air. The sealed tubing with emulsion is then placed in 37° C. thermostat together with the mounted syringe for 4 hours.

During the incubation at 37° C. the esterase enzyme mutants are produced in each droplet. As they are being synthesized some mutants may start to catalyze chemical conversion of the substrate nucleotides. Modified substrate nucleotide concentration is then established in each droplet. The number of modified substrate nucleotides may depend on the amount of catalytic biomolecules produced in each droplet.

After the incubation is over, the experiment is continued by preparing three 1 mL syringes mounted with 0.58 mm diameter needles with 0.56 mm diameter polytetrafluoroethylene tubing. First and second syringes are filled with 300 μL 1.5EA surfactant in HFE7500 fluorinated oil (v/v). The third syringe is filled with 300 μL HFE7500 fluorinated oil.

For this experiment reference nucleotides were to be 2'-deoxy-5-methylcytidine 5'-triphosphates. Phi29 polymerase can successfully incorporate them into the DNA strand during the nucleic acid synthesis.

Multiple displacement amplification (MDA) reaction mixture is then prepared according to Table 2.

The prepared MDA reaction mixture is then transferred to the third syringe. Fluids in all the three syringes are pushed out into the tubing by gently pressing the valve on the bottom and later placed into precision flow control pumps. The MDA reaction syringe must be placed vertically. Also, an ice jacket is required on the third syringe mounted in the pumps, to make sure reaction does not start before encapsulation.

The previously incubated IVTT reaction syringe is then taken out of the thermostat. The emulsion in the tubing is pushed until it reaches the end of the tubing.

The 30 um droplet merging device with Bi—Sn alloy electrodes is placed onto the microscopic table and high voltage cables are attached to the electrodes. The ends of the tubings are inserted to device inlets. Electrical impulse generator is then connected to high voltage source.

The tubing with previously incubated IVTT reaction together with its syringe is mounted into the precision flow control pump which is placed at a lower height than the microfluidic droplet merging device. The tubing with IVTT emulsion is inserted into the emulsion reinfusion inlet. A fresh 0.56 mm tubing without a needle is inserted into outlet of the device.

The MDA reaction mixture infusion is then initiated with flow rates of 100 µL/h for water phase and 270 µL/h for carrier oil in order to make 40 µL droplets.

Reinjected IVTT 10 µL droplets are infused at rates 30 µL/h for droplets and 300 µL/h for carrier oil.

The flow rates may be different in different experiments depending on voltage used with merging device, the initial IVTT droplet volume, surfactant used and other.

The freshly formed MDA and reinjected IVTT droplets are merged by applying square waveform current with 10 KHz frequency, 300-700 mVpp amplitude. The merging is continued until all of the IVTT droplets are infused and merged. The collected emulsion is placed in 30° C. for 5 hours to perform MDA reaction and then at 65° C. for 20 minutes to inactivate the polymerase.

After the IVTT reaction droplets had different amounts of modified substrate nucleotides. The amount of modified substrate nucleotides was based on the amount catalytic biomolecule produced in each droplet. Droplets that were merged with the droplets with modified substrate nucleotides contained the identical amount of reference nucleotides (2'-deoxy-5-methylcytidine 5'-triphosphate) in each droplet. Merged droplets then may contain a specific substrate nucleotide and reference nucleotide ratio.

As multiple displacement amplification reaction begins, the specific amount of modified substrate and reference nucleotides were incorporated into the DNA amplicon. Hence, in every droplet the DNA amplicon then may contain different amounts of modified substrate and reference nucleotides. DNA templates used for DNA amplification in different droplets are the same circular DNA templates from which catalytic biomolecules were produced.

After the reaction and inactivation steps are over, the emulsion can be broken by adding equal amount of 1H,1H, 2H,2H-Perfluoro-1-octanol (Pfo). The water phase is then cleaned with Ampure XP beads using bead volume of 0.4 water phase volume. After DNA purification, it is sequenced by nanopore using manufacturer's protocols. Nanopore sequencing in this case was chosen because of its ability to sequence long molecules, which removes the need for fragmentation and barcoding, and also can detect nucleotide modifications.

The sequencing data reveals plurality of details. First of all, it provides the information about the regulatory sequences of the initially prepared DNA library. Secondly, at the same time of retrieving regulatory sequence some of the nanopore post-processing algorithms (for example "SignalAlign" or "Nanomod" algorithms) may detect nucleotide modifications in the recorded signal. As mentioned earlier, the amplified DNA in each droplet contains a different amount of modified substrate and reference nucleotides. As some nanopore algorithms can detect nucleotide modifications, it enables accurate quantification of those nucleotides for each molecule. As the modified substrate nucleotide concentration in each droplet depends on the amount of catalytic biomolecule, the increased ratio of modified substrate nucleotide to reference nucleotide indicates increased ribosome affinity to a specific ribosome binding sequence and decreased ratio indicates about the decreased affinity.

In this way, using this invention, millions to billions (or more) of unique ribosome binding site sequences can be retrieved, together with the information about the particular ribosome binding affinity for each of the unique RBS sequence.

This example illustrated how described method can not only be used to gather information about catalytic biomolecule activity but also can explore the different properties of regulating sequences that modulate expression of catalytic biomolecule.

The invention claimed is:

1. A method for identifying a nucleic acid encoding an active catalytic molecule in a plurality of nucleic acids, comprising:
providing a plurality of compartments, each compartment comprising no more than one nucleic acid molecule encoding a catalytic biomolecule,
subjecting the compartments to conditions suitable for synthesis of the catalytic biomolecule,
providing substrate nucleotide to the compartments for said catalytic biomolecule,
wherein the substrate nucleotide cannot be incorporated into synthesized nucleic acid by polymerase,
subjecting said compartments to reaction conditions that allow catalytic molecule enzymatic activity to occur,
wherein said activity results in the modification of the substrate nucleotide, so that the nucleotide becomes suitable for incorporating into synthesized nucleic acid by polymerase,
providing into said compartments nucleic acid synthesis reaction mixture comprising reference nucleotides producing at least one copy of nucleic acid contained in the compartment,
wherein modified substrate nucleotide and reference nucleotide are incorporated into nucleic acid sequence by polymerase concurrently,
determining the ratio between reference nucleotide and modified substrate nucleotide in a newly synthesized nucleic acid,
wherein said ratio is indicative of catalytic activity of the catalytic biomolecule encoded by said nucleic acid.

2. The method according to claim 1, wherein the plurality of nucleic acids is obtained by a method selected from error-prone PCR, oligonucleotide-directed mutagenesis, assembly PCR, in vivo mutagenesis, cassette mutagenesis, recursive ensemble mutagenesis, exponential ensemble mutagenesis and site-specific mutagenesis or by lysis of a plurality of cells.

3. The method according to claim 1, wherein the compartment is a droplet, a microwell, a microtube, or an individual spot on a slide.

4. The method according to claim 1, wherein the reference nucleotide is 5-methyl-2'-deoxycytidine triphosphate.

5. The method according to claim 1, wherein substrate nucleotide is N4-benzoyl-2'-deoxycytidine triphosphate.

6. The method according to claim 1, wherein catalytic biomolecule is an enzyme, ribozyme or deoxyribozyme.

7. The method according to claim 6, wherein catalytic biomolecule is an esterase enzyme.

8. The method according to claim 1, wherein catalytic biomolecule catalytic activity is oxidoreduction, transfer of a chemical group, hydrolysis, bond cleavage other than hydrolysis or oxidation, changes within a single molecule, or joining two molecules with concomitant hydrolysis of the diphosphate bond in ATP.

9. The method according to claim 8, wherein catalytic biomolecule activity is cleavage of ester bond.

10. The method according to claim 1, wherein producing at least one copy of nucleic acid is performed by strand elongation, isothermal amplification reaction, or polymerase chain reaction.

11. The method according to claim 1, wherein ratio between reference nucleotide and modified substrate nucleotide in a newly synthesized nucleic acid is determined by single nucleic acid molecule analysis methods.

12. The method according to claim 11, wherein single nucleic acid molecule analysis method includes Nanopore sequencing, Bisulfite sequencing, Tethered Oligonucleotide-Primed sequencing, or Single Molecule Real Time (SMRT) sequencing.

13. The method according to claim 12, wherein single nucleic acid molecule analysis method is able to detect different nucleotide modifications.

14. The method according to claim 1, wherein synthesis of catalytic biomolecule is regulated by genetic regulatory sequences.

15. The method according to claim 14, wherein genetic regulatory sequence is ribosome binding site, promoter sequence, ribozyme, riboswitch, transcription enhancer, operator, repressor binding site, activator binding site, DNA binding site, terminator, repressor encoding gene, or activator encoding gene.

16. The method of claim 1, wherein providing substrate nucleotide to the compartments is done before or after the step of subjecting the compartments to conditions suitable for synthesis of the catalytic biomolecule.

17. A method for identifying a nucleic acid encoding an active catalytic molecule in a plurality of nucleic acids, comprising:
provided a plurality of compartments, each compartment comprising no more than one nucleic acid molecule encoding a catalytic biomolecule,
subjecting the compartments to conditions suitable for synthesis of the catalytic biomolecule,
providing substrate nucleotide to the compartments for said catalytic biomolecule,
wherein the substrate nucleotide can be incorporated into synthesized nucleic acid by polymerase,
subjecting said compartments to reaction conditions that allow catalytic molecule enzymatic activity to occur,
wherein said activity results in the modification of the substrate nucleotide, so that the nucleotide becomes no longer suitable for incorporating into synthesized nucleic acid by polymerase,
providing into said compartments nucleic acid synthesis reaction mixture comprising reference nucleotides
producing at least one copy of nucleic acid contained in the compartment,
wherein substrate nucleotide and reference nucleotide are incorporated into nucleic acid sequence by polymerase concurrently,
determining the ratio between reference nucleotide and substrate nucleotide in a newly synthesized nucleic acid,
wherein said ratio is indicative of catalytic activity of the catalytic biomolecule encoded by said nucleic acid.

18. The method of claim 17, wherein providing substrate nucleotide to the compartments is done before or after the step of subjecting the compartments to conditions suitable for synthesis of the catalytic biomolecule.

19. A method for identifying a nucleic acid encoding an active catalytic molecule in a plurality of nucleic acids, comprising:
providing a plurality of compartments, each compartment comprising no more than one nucleic acid molecule encoding a catalytic biomolecule,
subjecting the compartments to conditions suitable for synthesis of the catalytic biomolecule,
providing substrate nucleotide to the compartments for said catalytic biomolecule,
subjecting said compartments to reaction conditions that allow catalytic molecule enzymatic activity to occur,
wherein said activity results in the modification of the substrate nucleotide,
providing into said compartments nucleic acid synthesis reaction mixture comprising reference nucleotides
producing at least one copy of nucleic acid contained in the compartment,
wherein substrate nucleotide, modified substrate nucleotide and reference nucleotide are incorporated into nucleic acid sequence by polymerase concurrently,
determining the ratio between reference nucleotide, substrate nucleotide and modified substrate nucleotide in a newly synthesized nucleic acid,
wherein said ratio is indicative of catalytic activity of the produced catalytic biomolecule.

20. The method of claim 19, wherein providing substrate nucleotide to the compartments is done before or after the step of subjecting the compartments to conditions suitable for synthesis of the catalytic biomolecule.

\* \* \* \* \*

SEQUENCE LISTING

```
<160> NUMBER OF SEQ ID NOS: 2

<210> SEQ ID NO 1
<211> LENGTH: 1611
<212> TYPE: DNA
<213> ORGANISM: Artificial Sequence
<220> FEATURE:
<223> OTHER INFORMATION: Metagenomic origin

<400> SEQUENCE: 1
atgagctcac tttttattgg gcaagtattc gcgaagactc ccgaagtaca aacctccgac      60
ttgacaggta acaccacctg ctcgaacttg gttggaatgg tcatcccggc cgacgagatc     120
gggcttccta catcaggggc tacaatcaca tcagcgaccc ttaaaatcgt tgaagatggg     180
gctatcaaag acgccgaata ctgtgaagtg ttgggagcga ttcacccagt cgatccaacg     240
gcgcctgaca tcaactttca agtgaacctg ccaacaaatt ggaacaaaaa gttcttacag     300
tttggcggag gatatttcaa tggcaccgtc cgcacagggc ttggaaatcc tcctgccggc     360
```

```
gaccgtaagc tgggtaagaa cacccccttg gcacaagggt atgtgacctt cgggtcagac    420
agtggtaata gtaccgctcc gttggatgca tcttttggta tgaacgacga ggcattaaaa    480
aatttcgcgg gagatcagct gaaaaagact aaggatgtag ctttagcctt ggctaacgtc    540
cgttataatg ccgtaccgga tcaagtttac ttcgctggag gctccagggg cggtcgtgag    600
gggttgttca tcgtccagaa ttttcccgac gagtacgatg gagtcattag cgtataccc    660 gtattaaact ggatccccg tgctctgaag gataaccgcg atgctcaagc actttacaag    720
aatgacggag agggatggat ctccccagag gagaacgacc ttatcaacga gactgtattc    780
aaggcatgcg attcattgga tggcgtaaag gacggtatta ttagcaatac aagtgaatgt    840
gccgagaaag aagacaaaat tttggatacg ttaagcgagt ccctgtccga gaaacagatc    900
gaggttatta agagctttaa cgggccaatg gagtttgata tccagcttgc caacgatttt    960
acgacaatgc ctggttactc acagcttcag ggtgccgata ttggtcgttt gtttggtact   1020
cgcccaatcc ctggggtgcc cccgtcgtg agtgaatcgg tcggacacgt aatcgacgag   1080
caggacgctt taatgggcgt ctacagtgat caggtgatcc gttataagat cacgcgcaac   1140
ccagacttca atactcttac cttcgaccct aacgagtacc gtgaagaaat cttaaaggct   1200
tcaaacctgc tggacgtcac agaccctaat atcagtgaat tcgtgagaa tggggggaag   1260 ctgattttgg tgcatggcac cgaggatgaa atggttgcac cacaaggtac gagtgactat   1320
tatagtaaac tggtcaatga gttcggccaa gaatccttgg acgagtttgc acagtactac   1380
ttagtacctg gcttctcaca cggtggtggt aactttacaa tgtctgcaaa tttgttgggg   1440
gccttggacg cctgggtggt aaatggggat gtaccttcca acttggtggc ggaagatcag   1500
aactcggcga ctttcgggcg tactcgtccg ttgtgtgaat accctacata tccccagtac   1560
aatgggagtg gcgacgtaaa ttctgcggcc agttttacat gcttaaaagc a            1611
```

<210> SEQ ID NO 2
<211> LENGTH: 1611
<212> TYPE: DNA
<213> ORGANISM: Artificial Sequence
<220> FEATURE:
<223> OTHER INFORMATION: Metagenomic origin

<400> SEQUENCE: 2

```
atgagctcac tttttattgg gcaagtattc gcgaagactc ccgaagtaca aacctccgac     60
ttgacaggta acaccacctg ctcgaacttg gttggaatgg tcatcccggc cgacgagatc    120
gggcttccta catcaggggc tacaatcaca tcagcgaccc ttaaaatcgt tgaagatggg    180
gctatcaaag acgccgaata ctgtgaagtg ttgggagcga ttcacccagt cgatccaacg    240
gcgcctgaca tcaactttca agtgaacctg ccaacaaatt ggaacaaaaa gttcttacag    300
tttggcggag gatatttcga tggcaccgtc cgcacagggc ttggaaatcc tcctgccggc    360
gaccgtaagc tgggtaagaa cacccccttg gcacaagggt atgtgacctt cgggtcagac    420
agtggtaata gtaccgctcc gttggatgca tcttttggta tgaacgacga ggcattaaaa    480
aatttcgcgg gagatcagct gaaaaagact aaggatgtag ctttagcctt ggctaacgtc    540
cgttataatg ccgtaccgga tcaagtttac ttcgctggag gctccagggg cggtcgtgag    600
gggttgttca tcgtccagaa ttttcccgac gagtacgatg gagtcattag cgtataccc    660 gtattaaact ggatcccaa ggctctgaag gataaccgcg atgctcaagc actttacaag    720
aatgacggag agggatggat ctccccagag gagaacgacc ttatcaacga gactgtattc    780
aaggcatgcg attcattgga tggcgtaaag gacggtatta ttagcaatac aagtgaatgt    840
```

```
gccgagaaag aagacaaaat tttggatacg ttaagcgagt ccctgtccga gaaacagatc    900
gaggttatta agagctttaa cgggccaatg gagtttgata tccagcttgc caacgatttt    960
acgacaatgc ctggttactc acagcttcag ggtgccgata ttggtcgttt gtttggtact   1020
cgcccaatcc ctggggtgcc ccccgtcgtg agtgaatcgg tcggacacgt aatcgacgag   1080
caggacgctt taatgggcgt ctacagtgat caggtgatcc gttataagat cacgcgcaac   1140
ccagacttca atactcttac cttcgaccct aacgagtacc gtgaagaaat cttaaaggct   1200
tcaaacctgc tggacgtcac agaccctaat atcagtgaat tcgtgagaa tggggggaag    1260 ctgattttgg tgcatggcac cgaggatgaa atggttgcac cacaaggtac gagtgactat   1320
tatagtaaac tggtcaatga gttcggccaa gaatccttgg acgagtttgc acagtactac   1380
ttagtacctg gcttctcaca cggtggtggt aactttacaa tgtctgcaaa tttgttgggg   1440
gccttggacg cctgggtggt aaatggggat gtaccttcca acttggtggc ggaagatcag   1500
aactcggcga ctttcgggcg tactcgtccg ttgtgtgaat accctacata tccccagtac   1560
aatgggagtg gcgacgtaaa ttctgcggcc agttttacat gcttaaaagc a            1611
```